United States Patent [19]

Houston

[11] 4,392,235
[45] Jul. 5, 1983

[54] ELECTRONICALLY SCANNED X-RAY TOMOGRAPHY SYSTEM

[75] Inventor: John M. Houston, Schenectady, N.Y.

[73] Assignee: General Electric Company, Schenectady, N.Y.

[21] Appl. No.: 267,184

[22] Filed: May 26, 1981

Related U.S. Application Data

[63] Continuation of Ser. No. 66,932, Aug. 16, 1979, abandoned.

[51] Int. Cl.³ .............................................. G03B 41/16
[52] U.S. Cl. ...................................... 378/10; 378/124; 378/137
[58] Field of Search ....................... 250/445 T; 378/10

[56] References Cited

U.S. PATENT DOCUMENTS

| | | | |
|---|---|---|---|
| 4,045,672 | 8/1977 | Watanabe | 250/445 T |
| 4,135,095 | 1/1979 | Watanabe | 250/445 T |
| 4,199,684 | 4/1980 | Leunbach | 250/445 T |

Primary Examiner—Craig E. Church
Attorney, Agent, or Firm—Lawrence D. Cutter; James C. Davis, Jr.; Marvin Snyder

[57] ABSTRACT

An x-ray source for use in computerized tomographic applications focuses an electron beam on an arcuate anode ring to produce an x-ray beam which passes through a planar slice of the subject under study. Electromagnetic focusing and directing of the electron beam acts to produce the same effects as those produced by a single x-ray source which is mechanically rotated about the patient. Because it is very difficult to focus and to bend an electron beam having a cross section with other than cylindrical symmetry, and because it is highly desirable that the cross section of the electron beam have a rectangular cross section as it impinges upon the anode, an electromagnetic means is disposed adjacent the electron beam path between the anode and the beam bending coils to oscillatorily deflect the beam so that it effectively exhibits a substantially rectangular cross section, the long dimension of the rectangle always pointing toward the system axis. This configuration permits either a more intense x-ray source or, alternately, an x-ray source with a smaller projected spot size.

6 Claims, 5 Drawing Figures

ELECTRONICALLY SCANNED X-RAY TOMOGRAPHY SYSTEM

This application is a continuation of application Ser. No. 066,932, filed Aug. 16, 1979 now abandoned.

BACKGROUND OF THE INVENTION

This invention relates to computerized tomographic x-ray sources and in particular to such sources in which the x-ray beam direction is electronically controlled.

In a computerized tomographic imaging system, a beam of x-rays, often having a planar fan shape, is directed through the object under study. Various portions of the body absorb x-ray energy to a greater or lesser degree depending upon a number associated with each point in the body called the coefficient of x-ray absorption. Present day tomographic scanners typically exhibit a resolution in which such "point" is a square approximately 1 mm on a side. To gather sufficient information to determine the coefficient of absorption at points within the body, the x-ray beam is projected through the body from a plurality of different views. These views are typically spaced at regular angular increments in a plane. This plane determines the slice through the body for which an image is generated. This image is actually a pictorial representation of the x-ray coefficient of absorption associated with points in the body. In the resulting picture which is typically displayed on a cathode ray tube, the differing values of these coefficients are associated with different levels on a gray scale and/or with different colors to produce a false-color image.

Early computerized tomography scanners were only used for head scans because of their slow speed. Because the cranial organs undergo minimal movements, their motions posed no problem for these scanners. However, because of the great medical diagnostic advantages offered by computerized tomographic x-ray images, scans through other bodily organs are desired, and in particular scans through moving bodily organs, such as the heart, are highly desirable. For example, such heart scans are useful for determining the effectiveness of coronary artery bypass surgery. Because of the relatively rapid movement of the organs of the thorax and abdomen, it is desirable to collect absorption and data from several hundred views in less than 1 second. At present, relatively high speed computerized tomographic scanning is accomplished by disposing one or more conventional x-ray tubes along a circular rotating gantry which revolves about the patient at speeds of less 1 revolution per second. The radius about which these tubes revolve is approximately 1 meter and is determined essentially by human dimensional constraints. Because of this relatively large radius and because of the desire to have a rotation speed of approximately 1 revolution per second or less, unacceptably large g forces are exerted on the rotating x-ray source which itself often contains, for cooling purposes, a rotating anode.

To avoid the difficulties associated with mechanical rotation of the x-ray source, certain tomography systems employ an electronically scanned electron beam in order to allow much faster movement of the x-ray source point. Examples of certain features of such electronically scanned systems are found, for example, in U.S. Pat. No. 4,122,346 issued Oct. 24, 1978 to H. Enge and in U.S. Pat. No. 4,130,759 issued Dec. 19, 1978 to J. Haimson. A common feature of these systems is the relatively long distance between the electron gun source and the anode target. Because an electron beam comprises, by definition, particles which exhibit the same electrical charge, there is a natural tendency for the electron beam to openly diverge due to space charge forces. If the electron beam divergence is not controlled, insufficient electron beam energy arrives at the anode target. Moreover, the electron beam must be passed through bending coils which produce further aberrations from a convergent beam. Not only must the beam be non-divergent for proper bending and focusing, but the cross section of the electron beam should optimally be circular, that is, the beam should have cylindrical symmetry. In contrast, however, it is highly desirable that the electron beam cross section immediately prior to impingement upon the anode, be rectangular with the long dimension of the rectangle pointing toward the system axis. The rectangular beam cross section at this point is desirable for two reasons. First, because of the typical angle of impingement with the anode target, the cross section of the resultant x-ray beam source can be made to appear square, as viewed from the body or object under study. Second, an electron beam with a rectangular cross section distributes its energy more uniformly across the face of the anode target. Thus, by using a rectangular focal spot, a higher beam wattage is permissible without anode overheating, and the effective focal spot size (which causes loss of image spatial resolution if too large) is no larger than that of a square focal spot. However, if the electron beam, as emitted from an electron gun, were to have such a rectangular cross section, conventional focusing and bending coils would not properly function to produce the desired rectangular focal spot on the anode target.

SUMMARY OF THE INVENTION

In accordance with a preferred embodiment of the present invention, electromagnetic deflection means are disposed adjacent to the electron beam path between the anode ring and the bending and focusing coils to oscillatorily deflect the electron beam so that the beam thereafter effectively exhibits a substantially rectangular cross section. While magnetic deflection means may be employed, a high frequency electrostatic deflector exhibiting cylindrical symmetry about the central system axis is preferably employed. The frequency of voltage applied to the electrostatic deflector is chosen to be at least as high as the frequency with which different views of the subject under study are taken. The peak deflection voltage is selected so as to insure that the electron beam impinges upon a substantially rectangular portion of the anode target. While a sinusoidally varying deflection voltage may be employed, a sawtooth waveform is preferred since then the various portions of the rectangular anode spot receive the same average power. Additionally, while the preferred electrostatic deflection means may be disposed external to the housing containing the electron beams, it is preferred that the electrostatic deflection means be employed within the housing. The x-ray source of the present invention is readily employable in a tomography system which operates to produce high speed images of any desired human bodily organ.

DETAILED DESCRIPTION OF THE INVENTION

Figure 1:
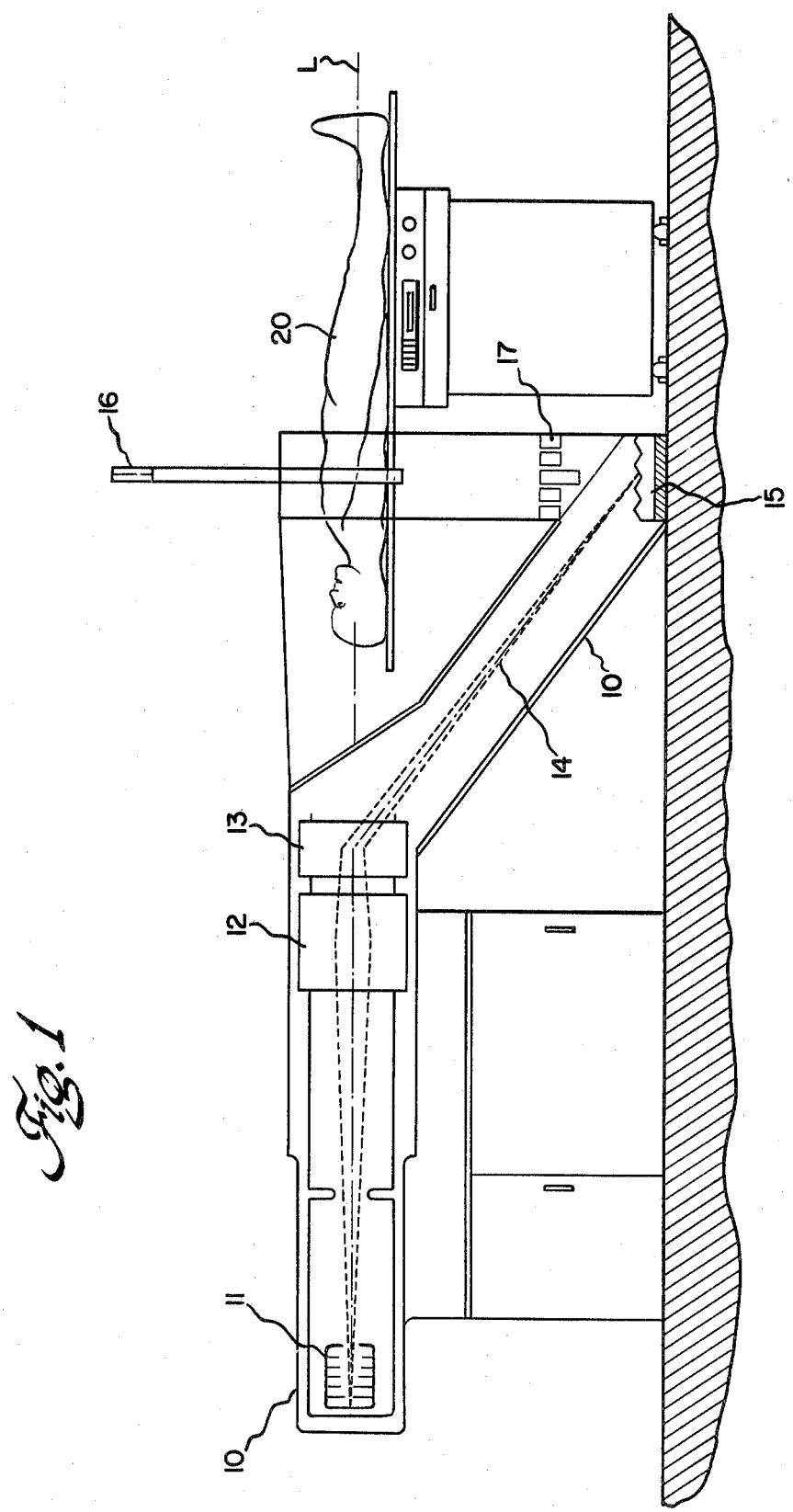
FIG. 1 is a cross-sectional side elevation view of a computerized tomography system employing an x-ray beam produced by electron scanning.

In FIG. 1 there is shown a computerized tomography imaging system employing an electronically scanned x-ray source. In such a system, mechanical rotation of the x-ray source is not required and the scanning to achieve data collection from differing views is performed electronically, primarily through the action of bending coils 13. The x-ray source and the apparatus for producing the electron beam are contained within vacuum housing 10. Disposed at one end of housing 10 is electron gun 11 which operates to accelerate a stream of electrons to an average kinetic energy of approximately 70 kev, corresponding to a peak beam voltage of 100 to 150 Kv. The cross section of the electron beam is circular. Because the electron beam comprises a stream of like-charge particles, there is a tendency for the beam to diverge as is suggested in FIG. 1. If such divergence were permitted to continue, the electron beam would not converge onto a focal spot on a targe anode. Accordingly, focus coil 12 is provided in accordance with conventional techniques, the coil 12 acts to cause a convergence of electron beam onto a relatively small target area of the anode. It is to be specifically noted at this point, that the electron beam cross section still exhibits cylindrical symmetry, that is, it has a circular cross section. After passage through focusing coil 12, the electron beam, typically having a current of approximately 500 milliamperes, passes through magnetic bending coil 13 which bends the beam by an angle of approximately 35° away from the central system axis L, as shown. The orientation of the bending magnetic field can be rapidly shifted; that is, there are two orthogonal sets of bending coils which are normally driven by sinusoidally varying currents which are 90° out of phase, so as to produce, at a constant bend angle of approximately 35°, a uniform rotation of the focal spot around the system axis L. That is to say, the focal spot uniformly rotates in a plane perpendicular to the system axis. Still exhibiting cylindrical symmetry, the electron beam 14 thereafter impinges upon the anode ring 15. As indicated in the figure, the entire traverse of the electron beam is contained within the vacuum housing 10, a cross section of which is shown in FIG. 1. The housing 10 is generally cylindrical in shape, particularly in that portion containing the electron gun. However, for a full appreciation of the shape of the vacuum housing 10, it is desirable to view FIG. 1 and FIG. 2 together.

Figure 3:
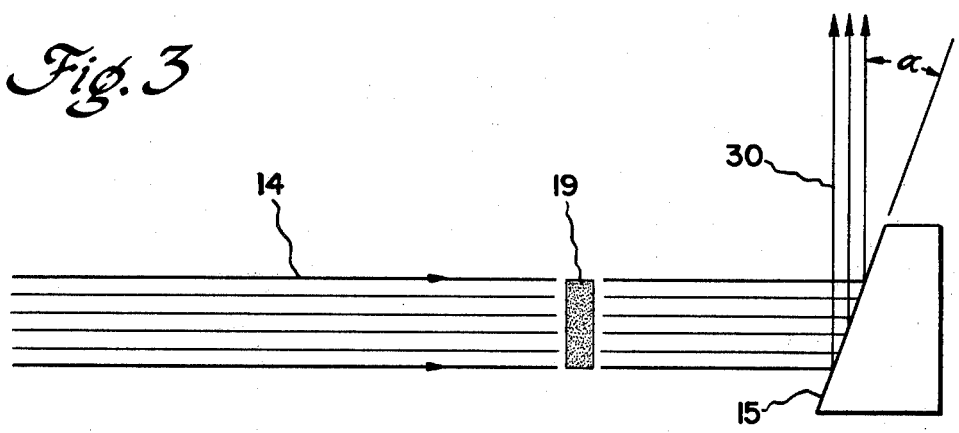
FIG. 3 is a diagram illustrating the desired geometry which should exist between the electron beam, the anode, and the resulting x-rays.

The electron beam 14, having been focused and bent by coils 12 and 13 respectively is caused to impinge upon targets affixed to anode rings 15 which typically comprise a metallic conductive material, the target portion of which is typically tungsten. The anode ring 15 is maintained at a high positive voltage with respect to the electron source. The particular anode ring illustrated in FIG. 1 has disposed thereon a sequence of four target regions, each of which may be employed independently. In operation, the electron beam can be made to impinge on any one of these four, or more, anode targets so as to produce an x-ray fan beam in any one of four parallel, distinct contiguous planes. This permits consecutive image slices to be generated, each of said slices being separate and perpendicular to central system axis L. FIG. 3, to be more particularly described below more completely illustrates the interaction between the electron beam and the anode to produce x-rays. However, in the x-ray source portion of the system in FIG. 1, the electron beam arrives at the anode having a small circular cross section. Because of the nature of this cross section and the angle of the anode target, the x-ray beam appears to be emanating from a source which has a squashed, elliptical shape. The minor axis of the apparent x-ray source ellipse is generally directed at a slight angle, toward the patient. The major axis of this ellipse is generally oriented in a direction parallel to a tangent to the anode ring structure. Because of the necessity for x-ray source collimators 17, a portion of the resulting x-ray beam signal is lost.

For purposes of illustration, the electron beam in FIG. 1 is shown as it impinges upon a lowermost target of the anode ring 15. However, anode ring 15 is actually an arcuate structure whose shape is more readily perceived in FIG. 2. In general, the electron beam focal spot rotates in response to signals applied to the bending coils 13 as to always impinge upon the targets affixed to the arcuate anode ring structure. These structures are angled with respect to the incident electron beam so as to produce a peak flux of x-ray photons directed up through source collimator 17 through the patient 20 and to detector ring 16 where the x-ray intensity level, having been modulated by absorption in the body 20, is converted to electrical signals for ultimate analysis by computer means which operate to generate the images as described above.

It is also to be noted that the shielding typically comprising a heavy metal conductive sheet is disposed between the subject 20 and the bending coils 13 for additional patient safety.

Figure 2:
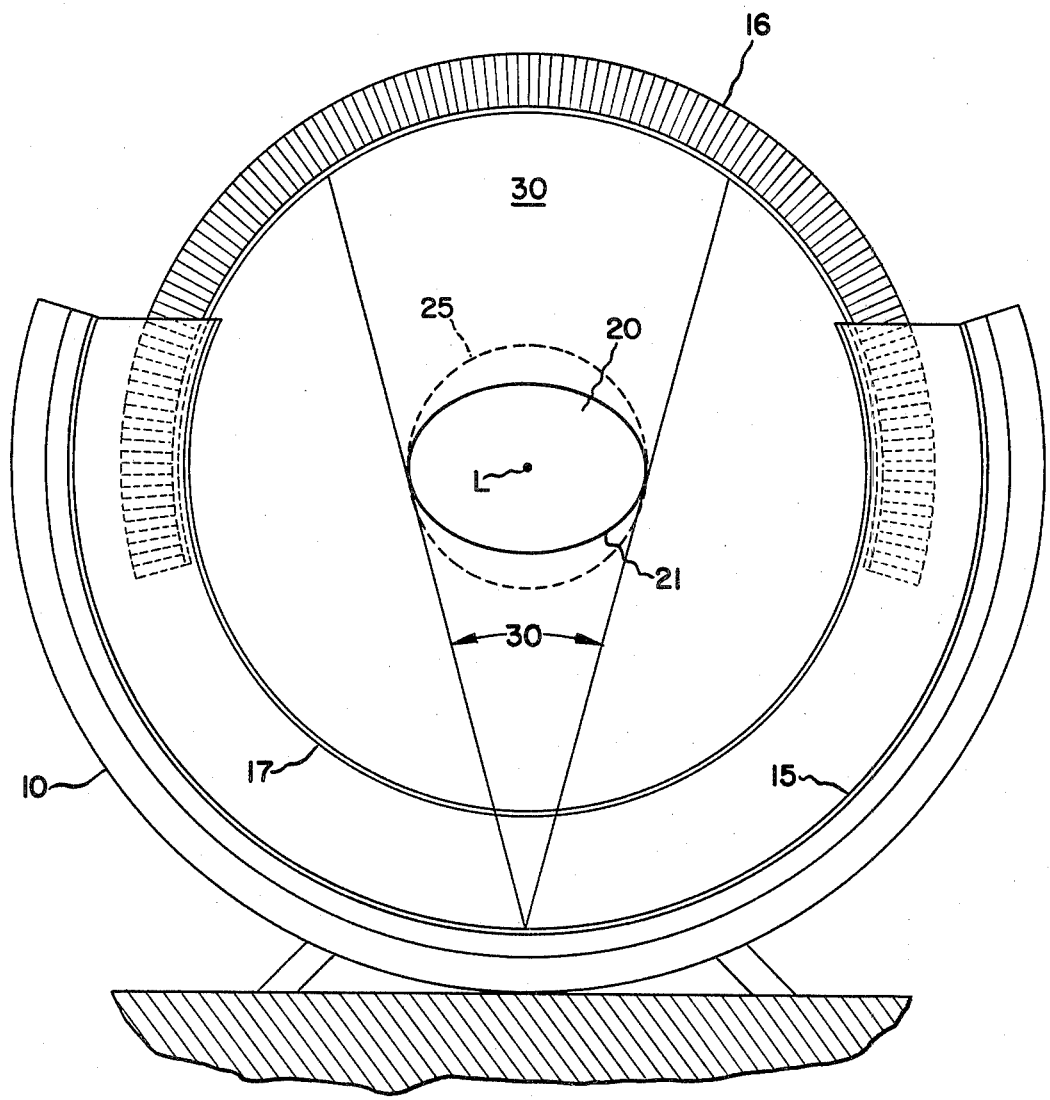
FIG. 2 is a front view of the apparatus shown in FIG. 1 detailing the relationship between the anode rings, the detector ring, and the body under study.

FIG. 2 illustrates the computerized tomographic imaging system of FIG. 1 as seen from the feet of the subject 20. Anode ring 15 and the vacuum housing 10 are clearly shown as arcuate structures from this perspective. In a typical tomographic imaging system for human patients, the anode ring 15 has a diameter of approximately 200 cm and extends for a circular angle of approximately 210° in a plane normal to the system axis L. This angular extension is sufficient to provide a full 180° scan with some overlap. The anode ring comprises a conductive metal and at least a portion of the anode ring is fashioned into angled target surfaces, preferably comprising a heavy metal such as tungsten. The x-rays that are produced by impact of the electrons on the anode target surface produce x-ray fan beams 30 having an approximate fan angle of 30° as shown. Such a fan beam is typically configured to subtend a field of view 25 having a diameter of approximately 50 cm. Within this field of view, typical patient cross section 21 is shown. The beam of x-ray photons having been selectively modulated by body portions of varying density thereafter impinges upon detector 16. The detector functions to convert the intensity levels of the impinging x-ray fan beam into directly related electrical signal levels. Such a detector may typically comprise crystals of bismuth germinate disposed between tungsten collimator plates and optically coupled to photomultipliers which produce the desired electrical signals. These electrical signals are then converted to digital form and are processed by digital computer means to produce numbers indicative of the coefficient of x-ray absorption exhibited by a small area of the subject under study. The size of this area determines the resolution of the imaging system which is typically approximately 1 mm × 1 mm.

FIG. 3 illustrates the desired relationship between an impinging electron beam 14 upon anode 15 giving rise to x-rays 30. The cross section of the electron beam in the figure is rectangular as shown by rectangular section 19. FIG. 3 is representative of the geometries employed in conventional x-ray tubes to help insure that the anode is not overheated. The length of the rectangular cross section is typically five to ten times its width. The x-rays are utilized at an angle $\alpha$, of between 6° and 13° as shown in FIG. 3, so that when viewed from the x-ray detector 16 the projected x-ray focal spot appears square. For example, for an electron beam cross section fives times its width, the projected focal spot appears perfectly square when $\alpha = 11.5°$. This method of using an electron beam with a rectangular cross section allows a suitable increase in x-ray output for a given degree of anode heating. For example, when the electron beam cross section is a rectangle with a length-to-width ratio of approximately 5, the allowable x-ray output increases by approximately five times. This is particularly true for brief, intensely loaded situations where the instantaneous heating of a local tungsten target surface is a limiting factor. In conventional x-ray tubes the rectangular cross section of the electron beam is readily assured by suitable collimation structures. However, in an electronically scanned tomography system as shown in FIG. 1, it is necessary that the electron beam possess a circular cross section for passage through the focusing and bending coils. More importantly, use of the bending coils produces undesirable effects if the beam has a rectangular cross section. A rectangular beam could be readily bent by the 35° angle, but the long axis of the rectangular focal spot would not in general always point at the system axis. Instead, as the focal spot is deflected along the 210° angle (measured in the plane perpendicular to the system axis), the long direction of the focal spot points in directions far removed from the system axis. Additionally, even if the cross section of the electron beam entering the bending magnetic field were uniformly circular, asymmetries caused by the bending method magnetic structures produce a focal spot which is essentially a 2×3 mm ellipse. Thus, even though a rectangular focal spot is highly desirable, this result is not achievable in the system described in FIGS. 1 and 2 alone.

Figure 4:
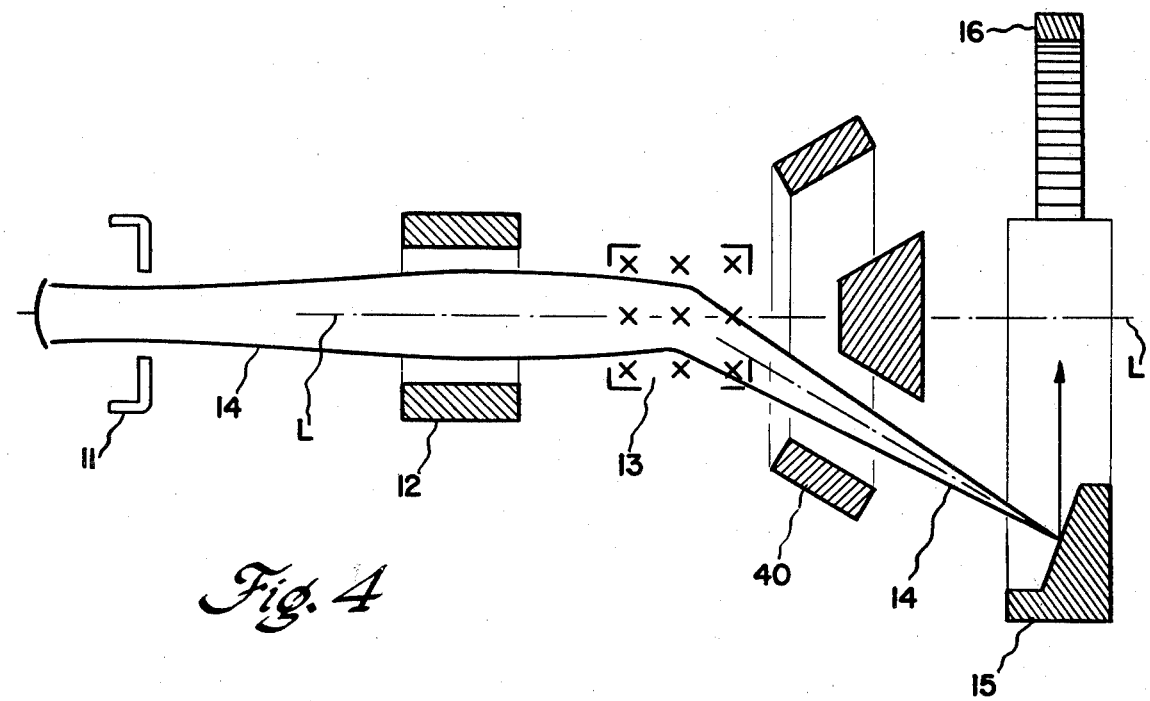
FIG. 4 is a cross-sectional side elevation schematic view illustrating the high frequency electrostatic deflector of the present invention.
Figure 5:
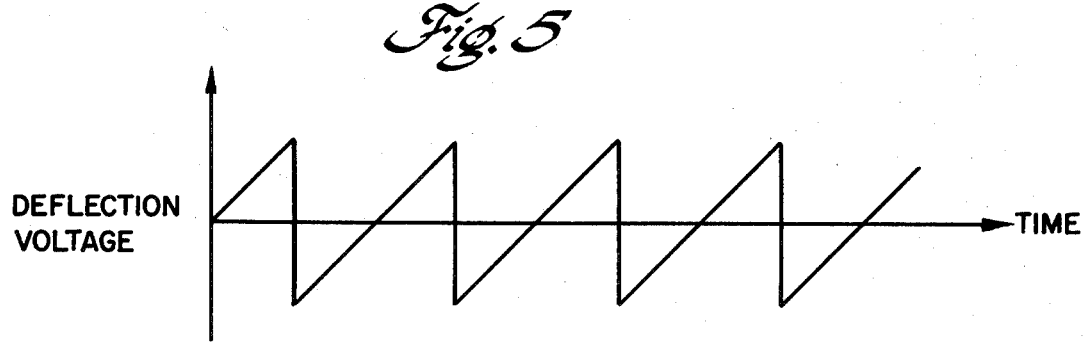
FIG. 5 is a graphical representation of the preferred deflector voltage.

In accordance with a preferred embodiment of the present invention, the benefits of a rectangular focal spot are achieved by adding a high frequency electrostatic reflector 40 as shown in FIG. 4. This deflector is cylindrically symmetrical about the system axis L, so that it, in effect, spreads out the power of the electron beam into a rectangular focal spot, the long dimension of which always points at the system axis L. The optimum voltage waveform for use with the electrostatic reflector 40 is a sawtooth wave with a fast return, as shown in FIG. 5. A sinusoidally varying voltage wave may also be employed but at a lesser anode power than with the sawtooth wave, because the anode locally overheats when the sinusodially varying deflection momentarily stops at the maxima and minima of the sine wave.

Although the preferred embodiment of the present invention employs an electrostatic structure to produce the deflection desired in the electron beam, it is also possible, although less desirable, to employ a time varying magnetic field to achieve similar results.

It is also desirable in the system illustrated in FIG. 4, that the deflection frequency be rapid enough so that the focal spot motion, due to the deflection, does not degrade the spatial resolution of the tomographic imaging system. In this respect, it is to be noted that such systems typically possess a sample period of approximately 40 microseconds. This sample period is the time between successive views, that is between successive locations of the x-ray focal spot along the 210° circular extension of the anode ring. If the deflection frequency is not synchronized with this sample period, then the deflection waveform period must be made small in comparison with the system sample period. Thus, for example, if the period of the deflection sawtooth is equal to 1 microsecond, the electron spot runs back and forth along the rectangular focal spot approximately forty times per view. Such a 1 MHz sawtooth waveform is readily achieveable with conventional electronics. However, if the deflection sawtooth waveform is synchronized with the clock controlling the sample period, then a slower deflection frequency may be used. That is, in such a situation, there is no problem with system resolution as long as a sample period is equal to an integral number of deflection waveform periods. However, care must be taken that the velocity of the electron spot does not slow down sufficiently so that the maximum instantaneous temperature of the tungsten anode rises above temperatures present at higher deflection frequencies.

By way of example, and not limitation, an electron focal spot having a 2 mm diameter may be spread out into a focal spot having a length of 10 mm and a width of 2 mm. For example, if the electron beam voltage is 120 kv and the electrostatic reflector is approximately 1 m from the tungsten anode and if the deflector has a length of 20 cm along the beam and a gap of 2 cm between the two halves of the deflector, the required peak-to-peak deflection voltage is approximately 230 volts which is readily achieved. Although this example does not consider relativistic effects, the required correction is not large and the resultant peak voltage is still readily achieveable by conventional electronics.

While it is possible to dispose the high frequency electromagnetic deflection means outside the vacuum housing, it is not necessary to do so and it is preferred that the means be disposed within the housing so as to provide greater control over the electron beam movement.

From the above, it may be appreciated that the present invention provides a tomographic imaging system in which there are no moving parts associated with the x-ray source and which permits either a more intense x-ray source or alternatively, an x-ray source with a smaller projected spot size, for greater resolution. Moreover, the x-ray source of the present system does not require the electronically scanned electron beam to have azimuthal velocities with respect to the arcuate anode ring, as apparently taught in the above-mentioned Haimson patent.

While this invention has been described with reference to particular embodiments and examples, other modifications and variations will occur to those skilled in the art in view of the above teachings. Accordingly, it should be understood that within the scope of the appended claims, the invention may be practiced otherwise than is specifically described.

The invention claimed is:

1. An x-ray apparatus for use in computed tomography comprising:

an electrode gun producing an electron beam having substantially circular cross section;

an arcuate anode ring;

means to focus and bend said electron beam so that said beam impinges on said anode ring at selectable points along its circumference;

an evacuable housing containing said electron gun and said anode ring;

electromagnetic deflection means disposed adjacent to said electron beam path, said deflection means being disposed along at least a portion of said electron beam path between said anode ring and said focussing and bending means to oscillatorilly deflect said electron beam in a radial direction with respect to said anode ring, so that after passing through said focussing and bending means said electron beam effectively exhibits an elongate cross section having substantially parallel sides and rounded ends, prior to impinging upon said anode ring, the long axis of said elongate cross section pointing toward an axis perpendicular to the plane containing said anode ring and passing through the center of said ring; and a plurality of x-ray detectors configured in a substantially annular array so as to receive x-ray radiation produced at said anode ring.

2. The x-ray source of claim 1 in which said oscillatory electromagnetic deflecting means is disposed within said housing.

3. The x-ray source of claim 1 in which said anode ring comprises a plurality of arcuate target rings, each such target rings oriented to direct the resultant x-ray beam into a distinct parallel plane.

4. The x-ray source of claim 1 in which oscillatory deflecting means is electrostatic.

5. The x-ray source of claim 1 in which said electromagnetic oscillatory deflection means employs a sawtooth deflecting signal.

6. A tomographic imaging system for producing images of a body, comprising:

an electron gun producing an electron beam having substantially circular cross section;

an arcuate anode ring;

means to focus and bend said electron beam so that said beam impinges on said anode ring at selectable points along its circumference;

an evacuable housing containing said electron gun and said anode ring;

electromagnetic deflection means disposed adjacent to said electron beam path, said deflection means being disposed along at least a portion of said electron beam path between said anode ring and said focussing and bending means, to oscillatorilly deflect said electron beam in a radial direction with respect to said anode ring, so that after passing through said focussing and bending means, said electron beam effectively exhibits an elongate cross section having substantially parallel sides and rounded ends, prior to impinging upon said anode ring, the long axis of said elongate cross section pointing toward an axis perpendicular to the plane containing said anode ring and passing through the center of said ring;

detection means which function to convert x-ray intensity levels, representative of x-ray absorption along x-ray beam paths, to electrical signals having corresponding levels; and means to process said electrical signals so as to produce a multidimensional image representing the coefficient of absorption at various points within said body.

* * * * *